United States Patent [19]
Novick et al.

[11] Patent Number: 5,618,700
[45] Date of Patent: Apr. 8, 1997

[54] IL-6 SPECIFIC MONOCLONAL ANTIBODIES, HYBRIDOMAS THEREFOR AND METHODS OF MAKING AND USING SAME

[75] Inventors: Daniela Novick; Michel Revel; Yves Mory, all of Rehovot; Menachem Rubinstein, Givat Shmuel; Eran Hadas, Rishon le-Zion, all of Israel

[73] Assignee: Yeda Research & Development Co. Ltd., Rehovot, Israel

[21] Appl. No.: 436,321

[22] Filed: Nov. 14, 1989

[30] Foreign Application Priority Data

Nov. 14, 1988 [IL] Israel .......................................... 88375

[51] Int. Cl.$^6$ .............................. C12P 21/08; C12N 5/20; C07K 16/24; C07K 1/22
[52] U.S. Cl. ................................... 435/70.21; 435/172.2; 435/335; 530/388.23; 530/413; 436/348
[58] Field of Search ..................................... 530/387, 413, 530/388.23; 435/240.27, 70.21; 436/172.2, 548

[56] References Cited

FOREIGN PATENT DOCUMENTS

| 0119859 | 3/1984 | European Pat. Off. . |
| 0312996 | 4/1989 | European Pat. Off. . |
| 2063882 | 6/1981 | United Kingdom . |

OTHER PUBLICATIONS

Novick et al. "Protides of the Biological Fluids; Proceedings of the Celloquium" vol. 32, Peeters, Ed., 1985 pp. 945–948.
Moks et al. Biotechnology 5:379–382, 1987.
Golub, "Immunology A Synthesis", Sinaur Assoc Inc 1987, pp. 19–20.
Johnstone et al. "Immunochemistry In Practice" Blackwell Sci Publ. 1987 pp. 207–240.
Goding, "Monoclonal Antibodies: Principles and Practice", Academic Press 1986, pp. 219–240.
Helle et al. J. Immunol Mtds 138:47–56, 1991.
Ida et al. Biochem Biophys Res. Comm. 165:728–734, 1989.
Van Heyningen et al., J. Immunol. Mtds vol. 62:147–153, 1983.
Novick et al., J. Gen Virol. 64:905–910, 1983.
Plückthun, Biotechnology 9:545, 1991.
Brakenhoff et al. J. Immunology 139(12):4116–21 Dec. 15, 1987.
Campbell *Monoclonal Antibody Technology* Elsevier Press 1984.
Kipps et al. Handbook of Expt'l. Immunology vol. 4, Weir et al. Eds. Blackwell Sci Publ., 1986.
Zilberstein et al. EMBO Journal 5(10) 2529–37, 1986.
Weissenbach et al. PNAS USA 77:, Dec. 1980, 7152–7156.
Van Damme et al. J. Immunology 140(5) 1534–41 Mar. 1, 1988.
Matsuda, T. et al. "Establishment of an interleukin 6(IL6)/B cell stimulatory factor 2–dependent cell line and preparation of anti–IL6 monoclonal antibodies", *Eur. J. Immunol.*, 18, 951–956 (1988).
Novick, D. et al., "Monoclonal antibody for purification and RIA of natural and recombinant human IFN–a, B and gamme", CA. No. 129976b, vol. 102, No. 15, p. 454, Apr. 15, 1985.
Suji, M. et al., "Monoclonal antibody to human beta interferon: Characterization and application", Biological Abstracts, No. 47888, vol. 85, No. 5, 1988.

*Primary Examiner*—Paula K. Hutzell
*Attorney, Agent, or Firm*—Browdy and Neimark

[57] ABSTRACT

The hybridoma 34-1 (CNCM I-813) which produces anti-human IL-6 monoclonal antibody 34-1 is disclosed. Methods of producing the monoclonal antibody and methods for affinity purification of human IL-6 using monoclonal antibody 34-1 are also described.

5 Claims, 12 Drawing Sheets

5,618,700

IL-6 SPECIFIC MONOCLONAL ANTIBODIES, HYBRIDOMAS THEREFOR AND METHODS OF MAKING AND USING SAME

FIELD OF THE INVENTION

The present invention relates to monoclonal antibodies to interleukin-6 (IL-6), previously named interferon-β2 (IFN-β2), to hybridoma cell lines producing said monoclonal antibodies and to a method for purification of IL-6 employing said monoclonal antibodies. It further relates to pharmaceutical compositions comprising said purified IL-6.

BACKGROUND OF THE INVENTION

Human IL-6 was first disclosed in GB 2,063,882 of the present assignee. Recombinant IL-6 expressed by CHO cells was described in European Patent Publication No. 220574 and Israeli Patent Application No. 81023 and recombinant IL-6 expressed by E. coli cells was disclosed in Israeli Patent Application No. 85204, all of the present assignee.

SUMMARY OF THE INVENTION

The cytokine interleukin-6 has multiple functions and activities and it is referred to also as interferon-B2 (IFN-B2) B-cell differentiation factor (BCDF) or B-cell stimulatory factor 2 (BSF-2), hybridoma growth factor (HGF), hepatocyte stimulatory factor (HSF), and 26 kDa protein.

The present invention provides, for the first time, monoclonal antibodies capable of specifically binding to IL-6 from different sources. They bind specifically to human natural IL-6 and/or to recombinant IL-6 expressed by mammalian, e.g. chinese hamster ovary (CHO) cells, or by bacterial, e.g., E. coli cells.

These monoclonal antibodies are produced according to the present invention from a hybridoma cell line obtained by fusion of myeloma cells with spleen cells from a mammal previously immunized with IL-6 or with a fusion protein comprising IL-6. Preferably, murine myeloma cells are fused with spleen cells from a mouse immunized with a fusion protein comprising IL-6, e.g. Protein A—IL-6 fusion protein.

The fusion of the cells to obtain the hybridoma is done in the presence of a suitable fusion promoter of those known in the art. The fused cells are then cultured in separate wells and the supernatant of each well is tested for the presence of the desired monoclonal antibody capable of specifically binding to IL-6. This screening is preferably done with IL-6 from a different source than the IL-6 used for the immunization of the mice. Thus, if a Protein A—IL-6 fusion protein expressed by E. coli cells is used to immunize the mice, then the screening of the monoclonal antibodies is performed with IL-6 produced by chinese hamster ovary (CHO) cells.

The positive clones producing the desired antibodies are then selected and subcloned and either cultured in a suitable growth medium or injected into mice, and the desired monoclonal antibodies are then recovered from the supernatant of the cultured cells or from the ascitic fluid of said mice, respectively.

In a preferred embodiment, the development of monoclonal antibodies to human IL-6 was achieved through the following steps:

(a) production of a Protein A—IL-6 fusion protein in E. coli;

(b) purification of the Protein A—IL-6 fusion protein by affinity chromatography on IgG Sepharose column;

(c) injection of the purified Protein A—IL-6 fusion protein into mice and production of anti-IL-6 monoclonal antibodies, and (d) screening of the monoclonal antibodies with a recombinant IL-6 produced in chinese hamster ovary (CHO) cells.

In order to prevent cross-reaction of the Protein A and of any E. coli contaminants in the antigen preparations used for injection with some of the monoclonal antibodies during the screening, two types of human recombinant IL-6 were used for the development of specific monoclonal antibodies. The first recombinant IL-6 was produced in E. coli and used for immunization, the second one was produced in CHO and it did not contain Protein A or any E. coli antigen. This IL-6 preparation was used for screening.

According to the invention, there is described the construction of a plasmid for the expression in E. coli of a fused Protein A—IL-6 protein and its use for obtaining monoclonal antibodies. The complete translated sequence of the cDNA coding for human IL-6 (see European Patent Publication No. 220,574, FIG. 1) was fused, in phase, to the 3' end of a portion of the gene coding for Protein A.

The protein A gene has three genetically distinct parts (Uhlen et al. (1984) J. Biol. Chem. 259, pp. 1965). FIG. 1 shows the three regions of the protein A structural gene: the signal sequence (S), an affinity tail containing five homologous IgG-binding domains (E-C) and a cell wall/membrane associated region (X). The protein A fusion vector (Pharmacia) contains only the affinity tail of the staphylococcal protein. After fusing the coding sequence of the IL-6 with the coding sequence for the staphylococcal Protein A affinity tail, the resulting fusion protein was purified in a single affinity chromatography step on IgG Sepharose 6 Fast Flow (FF).

For efficient expression in E. coli the hybrid gene was fused to the strong lambda $P_R$ promoter.

After six injections of the purified protein into mice, positive sera were tested for their binding titer in a solid phase radioimmunoassay (SRIA) and for the specificity of binding by Western blots. For the SRIA, crude supernatants of CHO cells, harboring a plasmid containing the human IL-6 gene under the control of the SV40 early promoter and expressing high levels of this gene but no Protein A or any bacterial antigen, were bound to a solid support and reacted with supernatants of the hybridomas and with [$^{125}$I] goat antimouse antibodies. Spleen cells derived from a mouse showing the highest binding titer (dilution 1:2500) were fused to mouse myeloma cells. They hybridomas were screened by the SRIA and several positive clones were isolated and characterized.

The DNA vectors used in this invention were construced by standard procedures. Plasmid DNAs were purified by banding in CsCl-ethidium bromide gradients. DNA restriction fragments separated by electrophoresis in agarose or polyacrylamide gels were purified on DE-52 columns. Restriction endonucleases (Boehringer, New England Biolabs), T4 DNA ligase (New England Biolabs), the large fragment of E. coli DNA polymerase (Boehringer) and T4 polynucleotide kinase (Pharmacia), were used as recommended by the suppliers. E. coli transformation was carried out with frozen competent bacteria (D. A. Morrison, (1979) Methods Enzymol. 79, pp. 326–331) using strains HB101 ATCC 33694, and N4830-1 (Gootesman et al. (1980) J. Mol. Biol. 140, p. 57).

DETAILED DESCRIPTION OF THE PREFERRED EMBODIMENTS

EXAMPLE 1

Construction of Plasmids pRIβ₂802 and pRIβ₂604

Figure 1:
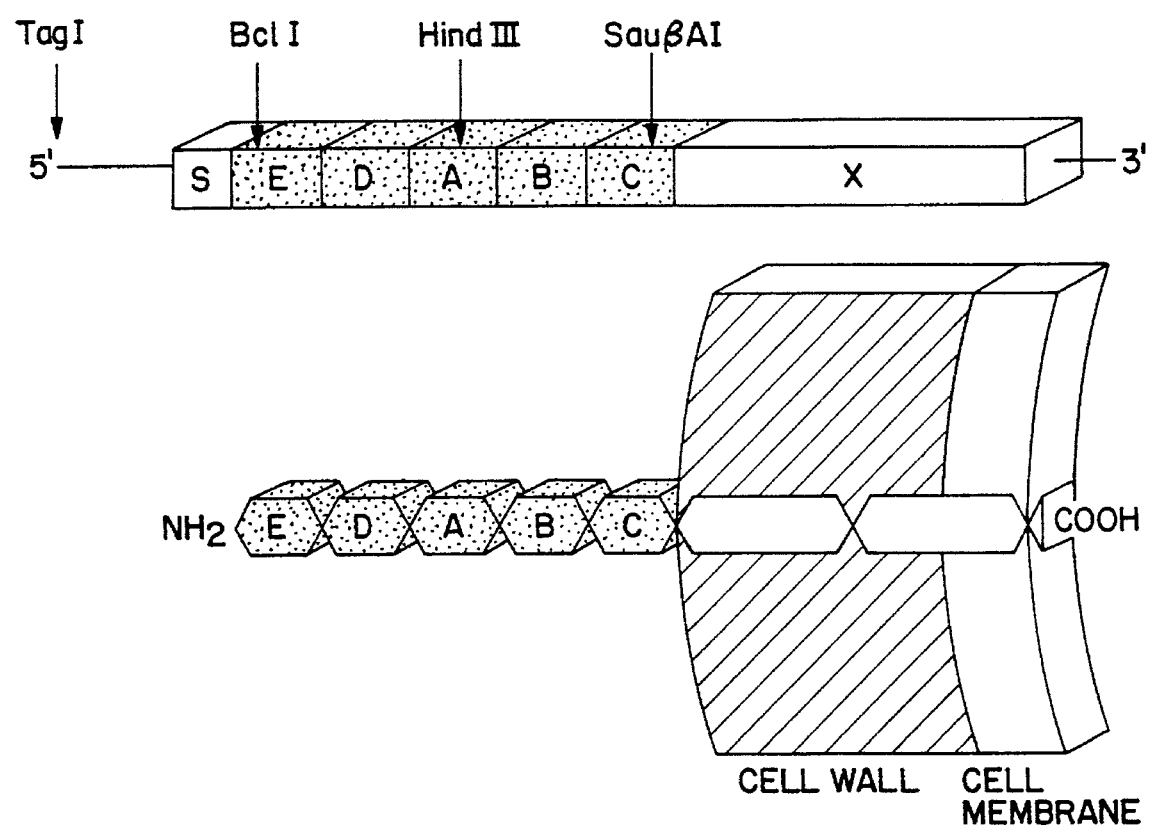
FIG. 1 shows the various regions of the protein A gene and the corresponding protein.
Figure 2A:
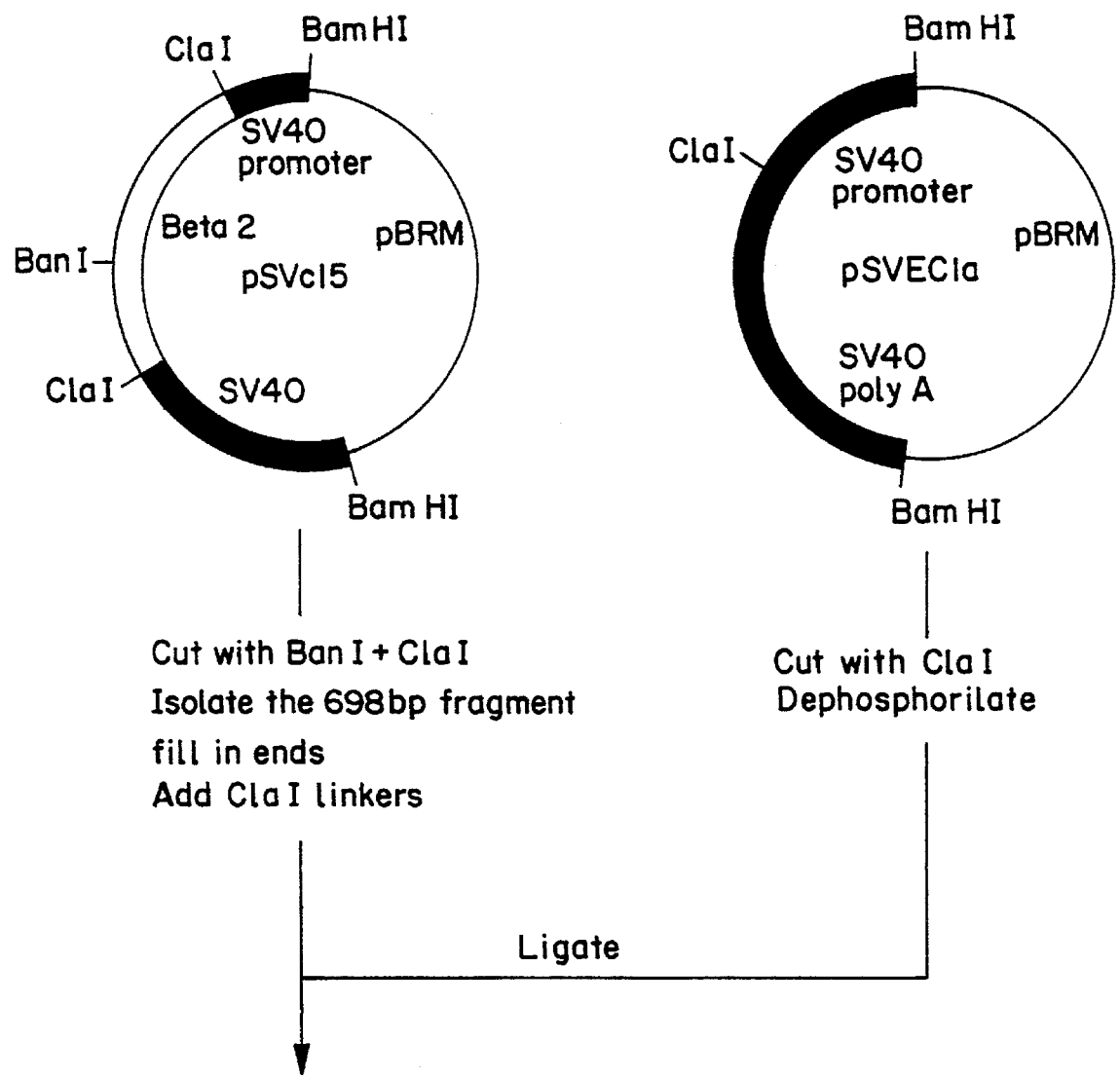
FIG. 2 is a schematic graphically summarizing the various steps in the construction of expression vector pSVβ₂HB.
Figure 2B:
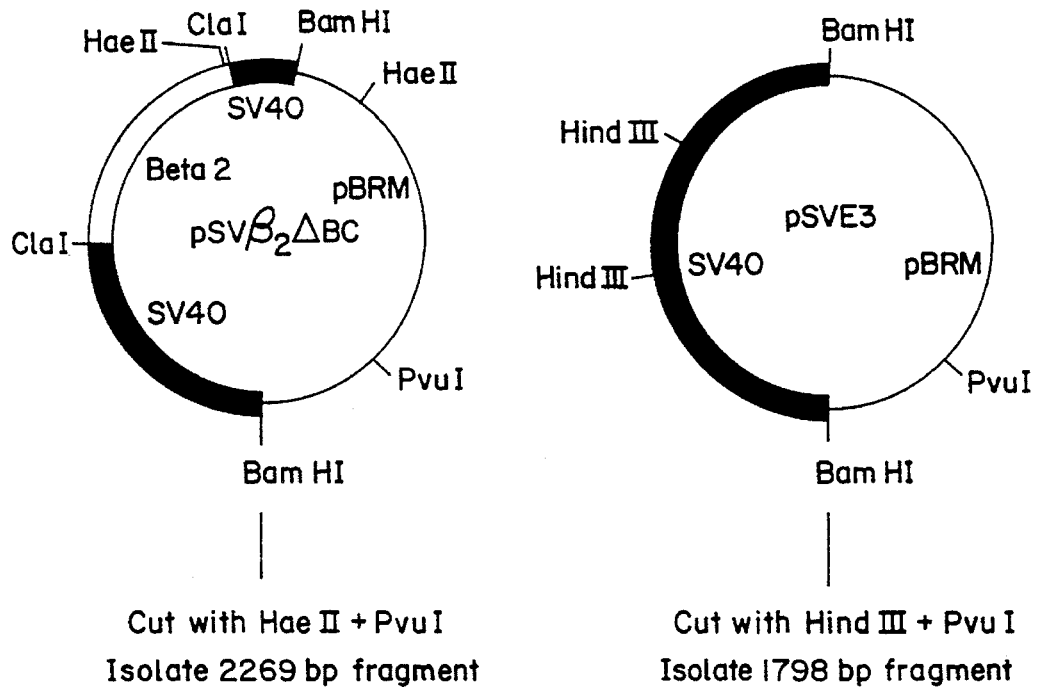
Figure 2B:
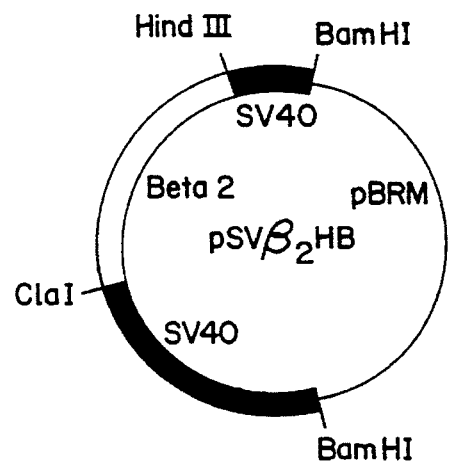
Figure 3A:
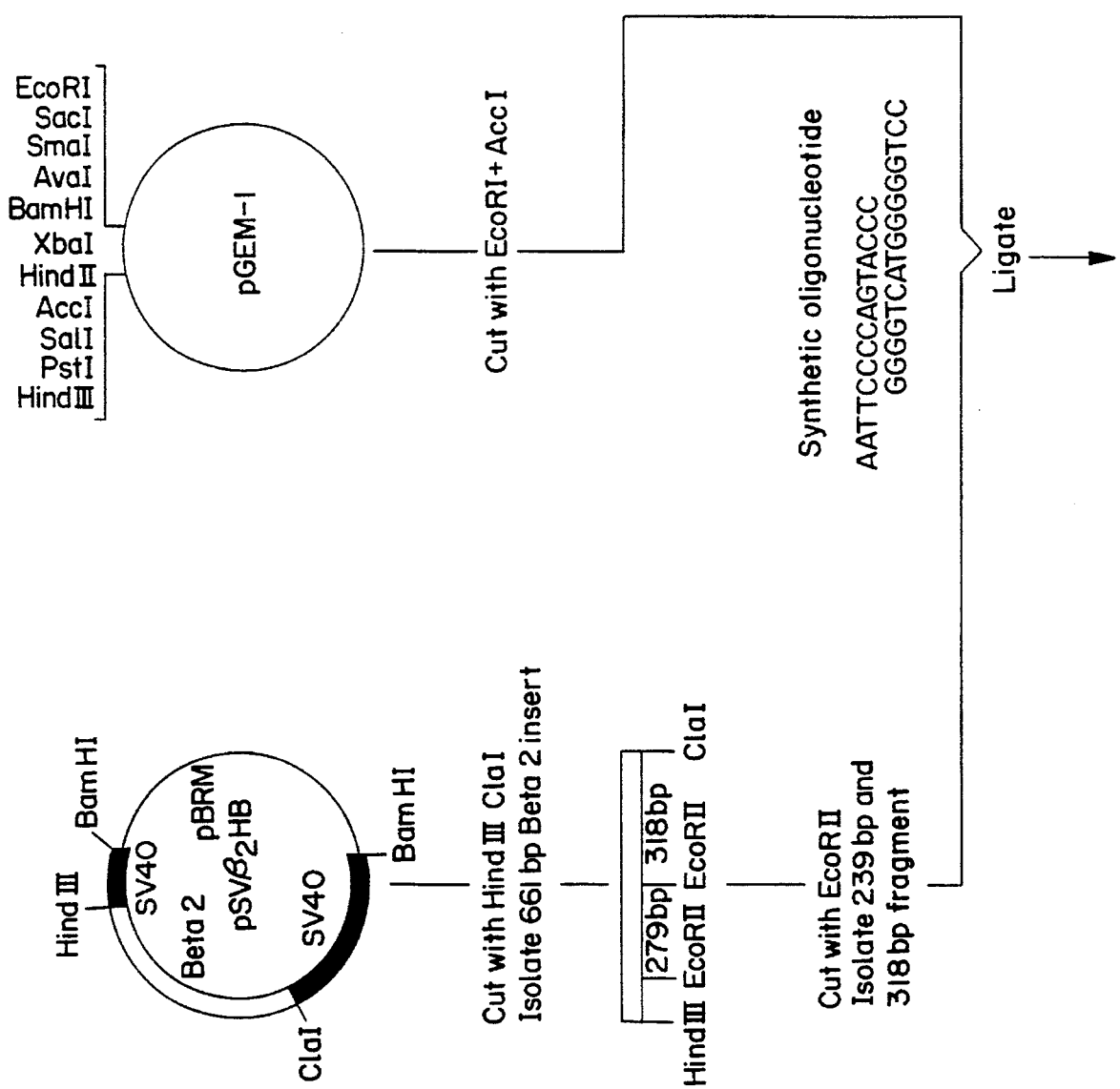
FIG. 3 is a schematic graphically summarizing the various steps in the construction of plasmids pRIβ₂604 and pRIβ₂802.
Figure 3B:
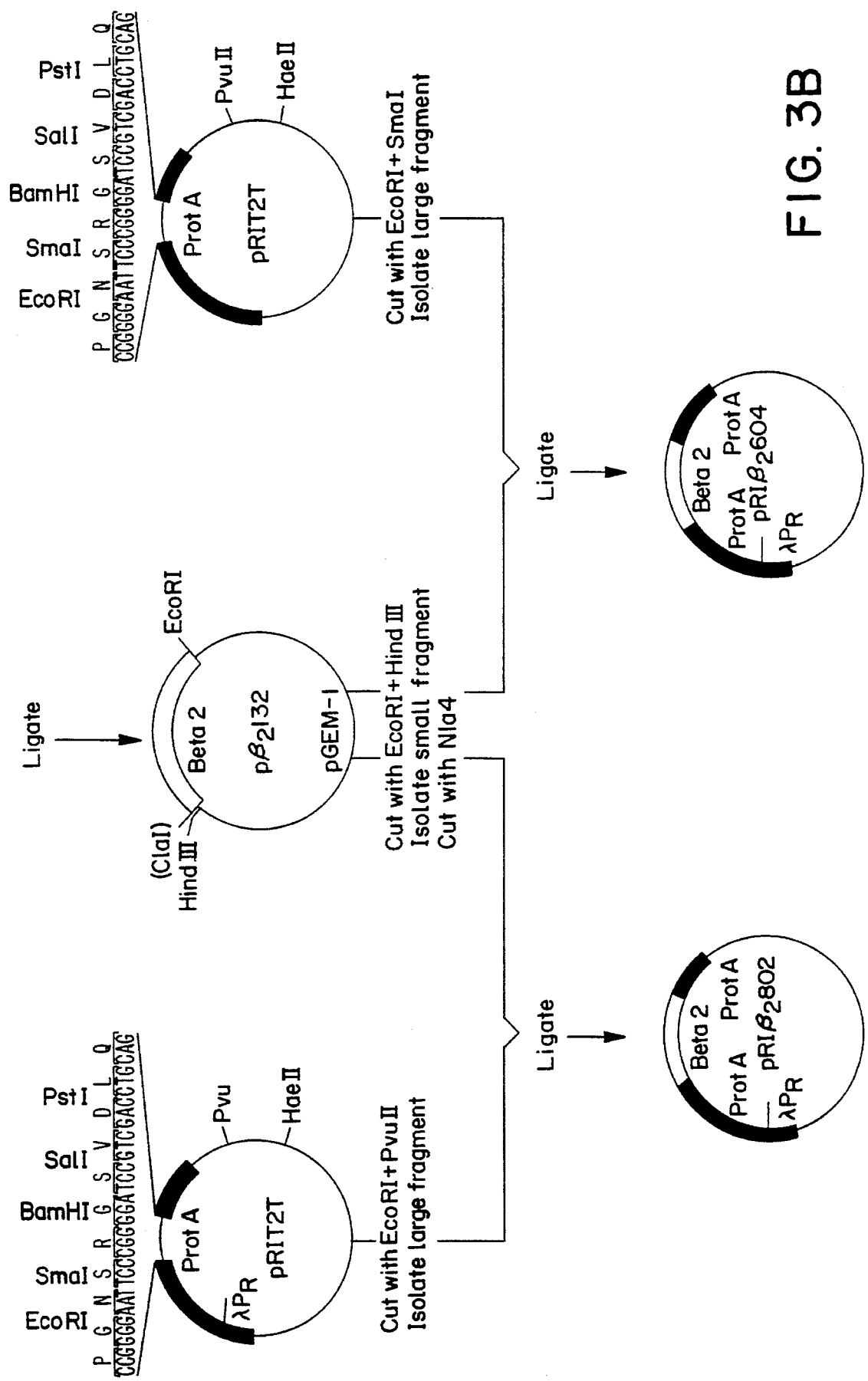

FIG. 2 describes the construction of expression vector pSVβ2HB and FIG. 3 summarizes graphically the various steps in the construction of plasmids pRIβ₂802 and pRIβ₂604. The cDNA fragment coding for IL-6 was excised from plasmid pSVβ₂HB as a 661 bp HindIII/ClaI fragment. Plasmid pSVβ₂HB is one of the vectors used for constitutive expression of this gene in CHO cells under the strong SV40 early promoter. This plasmid was derived from plasmid pSVIFβ₂ (A. Zilberstein et al. (1986) EMBO J. 5, pp. 2529–2537) by removing all the 5' and 3' non-coding sequences of the cDNA by standard cloning techniques.

In the coding sequence of the IL-6 cDNA there are four EcoRII sites. These sites are located 44, 56, 93 and 332 bp from the initiator ATG codon which is located 11 nucleotides from the 5' end. The first two sites are located between the initiator ATG and the first proline of the mature protein, the third and fourth EcoRII sites are located 9 bp and 248 bp downstream from the first proline codon.

The 661 bp insert of plasmid pSVβ₂HB was digested with EcoRII and the resulting five fragments were separated on a preparative agarose gel. The three small fragments of 55, 12 and 37 bp, coding for the signal peptide sequence and for the first three amino acids of the mature protein were discarded. The two fragments of 239 and 318 bp were recovered from the gel. In order to restore the sequence coding for the first amino acids and to maintain the Protein A frame, a double stranded oligonucleotide was synthesized, which has the sequence shown in FIG. 3. This oligonucleotide was ligated together with the 239 bp and 318 bp fragments into plasmid pGEM-1 previously digested with EcoRI and AccI. The resulting plasmid was called pβ₂132.

Plasmid pβ₂132 contains the whole IL-6 sequence preceded by an asparagine and a serine codon within the multiple coding site of plasmid pGEM-1. The asparagine and serine codons are the two codons at the unique EcoRI site (at the 3' end of the Protein A gene) of plasmid pRIT2T that was used for subsequent cloning. Plasmid pβ₂132 was digested with EcoRI and HindIII in order to isolate the complete cDNA sequence which was introduced into plasmid pRIT2T digested either with EcoRI and PvuII or with EcoRI and SmaI restriction endonucleases for the obtention of the plasmids of the invention pRIβ₂802 and pRIβ₂604 (FIG. 3).

Figure 4:
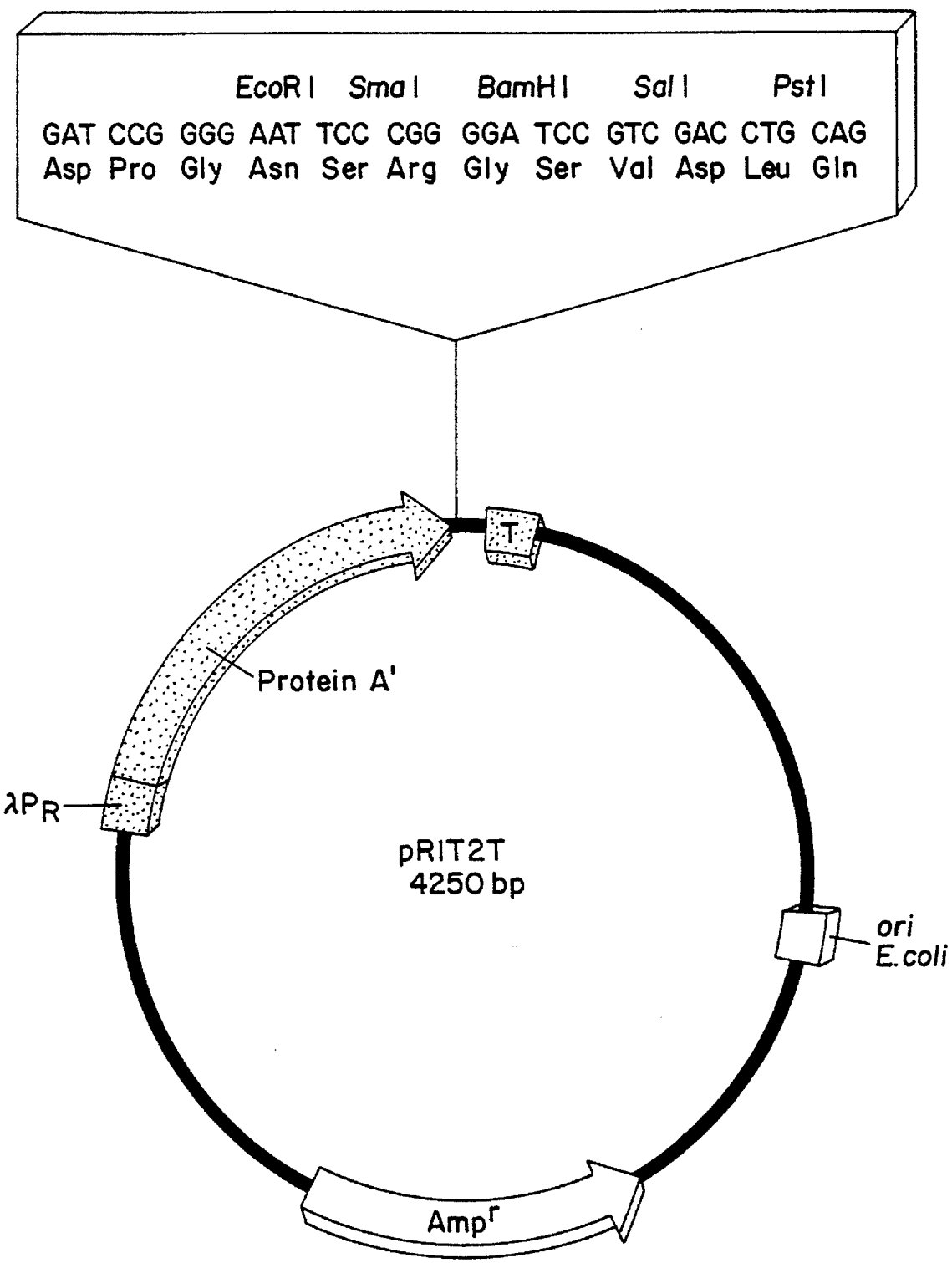
FIG. 4 shows the construction of the plasmid of the PRI2T Protein A fusion vector.

The plasmid pRIT2T contains the protein A affinity tail and is designed for temperature-inducible expression of intracellular fusion proteins in *E. coli*. The host cell for this plasmid is *E. coli* N4830-1, containing the temperature-sensitive lambda $cI_{857}$ repressor. When the temperature is shifted from 30° C. to 42° C., the repressor is inactivated and the $P_R$ promoter is turned on, thus initiating expression of the fusion protein conjugate.

pRIT2T is derived from pCL10 YT, pSPA11 and pEMBL9 (pUC8). The exact localization of the different fragments, with corresponding map units, are shown in FIG. 4 (Plasmid map of pRIT2T Protein A fusion vector). The vector contains the thermoinducible lambda $P_R$ promoter and the first 12 codons of a lambda cro/lacZ gene fused to a truncated form of the staphylococcal Protein A gene (nucleotides 385–1103) which includes the IgG binding domains. Both the Protein A promoter and signal sequence have been removed. The 3'-terminal region of the Protein A gene, nucleotides 1550–1920 and approximately 300 additional nucleotides from the non-coding region, is fused downstream of the multiple cloning site (MCS) and provides transcription termination signals. Translation termination signals are present in two reading frames immediately downstream from the MCS (map position 0.84) and in the third reading frame further downstream (map position 0.90). The pBR322 origin of replication and the ampicillin resistance gene are present for replication and selection in *E. coli*. Five unique restriction sites, the same as for pUC9, are contained within the MCS: EcoRI, XcyI (SmaI, XmaI), BamHI, SalI (HincII, AccI) and PstI. The plasmid size is 4 250 base pairs.

EXAMPLE 2

Obtention of transformed *E. coli* cells

Frozen competent *E. coli* cells were transformed with the replicable recombinant plasmids pRIβ₂802 and pRIβ604 by well-known methods (see D. A. Morrison (1979) Methods Enzymol. 79, pp. 326–331). The transformation of strain *E. coli* N4830-1 with the recombinant plasmid pRIβ₂802 gave origin to the new microogranism *E. coli* N4830-1/pRβ802. The transformation of strain *E. coli* N4830-1 with the recombinant plasmid pRIβ604 gave origin to the new microorganism *E. coli* N4830-1/pRβ604.

EXAMPLE 3

Production of the Protein A-IL-6 Fusion Protein and its purification

In order to grow the *E. coli* cells obtained in Example 2 to induce the expression of the Protein A-IL-6 fusion protein and to prepare an extract suitable for affinity chromatography purification, the following procedure was adopted:

Diluted cell cultures were grown overnight at 30° C. in M9 medium containing ampicillin to early stationary phase, then incubated at 42° C. for 90 minutes, cooled and harvested by centrifugation. After repeated resuspension and centrifugation, 20% SDS was added to a final concentration of 1% and 10M urea to a final concentration of 8M, and the extract was dialyzed against TST (50 mM Tris pH 7.6, 150 mM NaCl and 0.05% Tween 20).

For the purification, the clear supernatant after dialysis was applied to the IgG Sepharose 6 Fast Flow (FF) equilibrated column. After loading on the column the gel is washed with 10 bed volumes of TST and 2 bed volumes of 5 mM $NH_4COOH$, pH 5.0. The bound protein is eluted with 0.5M $NH_4COOH$, pH 3.4 and lyophilized directly without prior dialysis.

EXAMPLE 4

Immunization of mice and cell fusion

Three-month old female Balb/c mice were first injected with the partially purified Protein A-IL-6 fusion protein obtained in Example 3 (10 μg/mouse emulsified in complete Freund's adjuvant). Three weeks later the mice were given a subcutaneous boost with the fusion protein in solution. Four additional injections were given at 10 days intervals. The mouse showing the highest binding titer (Table 1) and the strongest signal in Western blot analysis received an intra-peritoneal injection of the fusion protein and three days later its splenic lymphocytes ($150 \times 10^6$ cells) were fused with $30 \times 10^6$ NSO/1 myeloma cell line. The fused cells were distributed into microculture plates ($3 \times 10^4$ cells/well) and selection for hybridoma growth was in DMEM supplemented with 10% FCS, 1 mM pyruvate, 2 mM glutamine, penicillin-streptomycine 100 u/ml, fungizone 1 μg/ml and containing HAT. Hybridomas that were found to secrete anti-IL-6 antibodies were cloned and recloned by the limiting dilution technique.

EXAMPLE 5

Screening for IL-6 specific hybridomas

Hybridoma supernatants were tested for the presence of anti-IL-6 antibodies by a solid phase RIA (SRIA). PVC microtiter plates (Dynatech Laboratories, Alexandria, Va.) were coated with a crude, serum-free supernatant of CHO cells secreting IL-6 (80 μg/well). Following an incubation of 2 hrs at 37° C. or 16 hrs at 4° C. the plates were washed twice with PBS containing BSA (0.5%) and Tween 20 (0.05%) and blocked in washing solution for 2 hrs at 37° C. Hybridoma culture supernatants (50 μg/well) were added and the plates were incubated for 4 hrs at 37° C. The plates were then washed three times with the washing solution and $^{125}$I-goat anti-mouse (Fab')$_2$ (50 μl, $10^5$ cpm) was added for further incubation of 16 hrs at 4° C. The plates were washed 4 times and individual wells were cut and counted in a gamma counter. Samples giving counts that were at least four times higher than the negative control value were considered positive (Table 1).

TABLE 1

| Screening of hybridomas by SRIA | | |
|---|---|---|
| Sample | dilution | cpm |
| Immune serum (mouse) | 1:4000 | 2800 |
| negative control (mouse) Hybridoma | 1:4000 | 100 |
| 12 | | 4000 |
| 12 | 1:125 | 300 |
| 27 | | 1100 |
| 28 | | 2200 |
| 34 | | 6200 |
| 34-1 | 1:2500 | 1000 |

TABLE 1-continued

| Screening of hybridomas by SRIA | | |
|---|---|---|
| Sample | dilution | cpm |
| 38 | | 2600 |
| 48 | | 1500 |
| 102 | | 1200 |
| 117 | | 1400 |
| 123 | | 1100 |
| 125 | | 1600 |
| 132 | | 5400 |
| 136 | | 2700 |
| 154 | | 1500 |
| 157 | | 2400 |
| negative hybridoma | | 200 |
| Ascitic fluid | 1:62,000 | 1400 |
| Ascitic fluid negative | 1:12,000 | 300 |

As can be seen from Table 1, fourteen anti IL-6 hybridomas were selected using the solid phase RIA (SRIA). Hybridoma No. 34-1, sub-cloned from hybridoma 34, was further characterized and was found to belong to IgG1 class. Hybridoma 34-1 (HB2 34-1) was deposited with the Collection Nationale des Cultures de Microorganismes—CNCM, Institute Pasteur, Paris, on 14.11.88. It was accorded No. I-813.

Hybridoma 34-1 was found suitable for Western blotting and for affinity purification of both natural and recombinant IL-6 expressed by E. Coli and by CHO cells. It was used in the following experiments.

EXAMPLE 6

Western blotting

Figure 5:
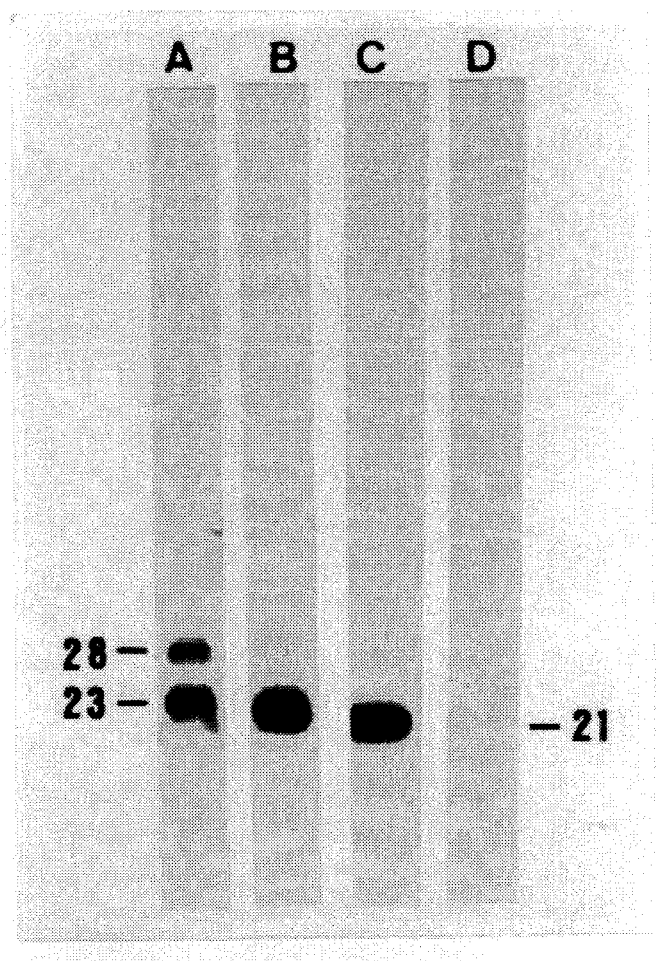
FIG. 5 shows the results of binding of antibody no. 34-1 to various IL-6 preparations in accordance with Example 6. Lane A is natural IL-6; lane B is recombinant IL-6 in CHO cells; lane C is recombinant IL-6 of *E. coli* cells; and lane D is recombinant IFN-β1 of CHO cells (comparison).

Samples of crude preparations of either natural or recombinant IL-6 expressed by CHO and E. coli cells were analyzed by SDS-PAGE under reducing conditions and electroblotted onto nitrocellulose sheets (BA85, Schleicher and Shuell). Following electroblotting the sheet was incubated overnight with a blocking buffer (5% non-fat milk in PBS containing 0.05% Tween 20 and 0.02% sodium azide) and then for 2 hrs at room temperature with the anti-IL-6 antibody No. 34-1. Following washing in 0.05% Tween 20 in PBS, the nitrocellulose was incubated for 3 hrs at room temperature with $^{125}$I-goat anti-mouse serum ($0.7 \times 10^6$ cpm/ml in the blocking buffer). The sheet was then washed, dried and autoradiographed. The results are shown in FIG. 5: Lane A: natural IL-6; Lane B: recombinant IL-6 of CHO cells; Lane C: recombinant IL-6 of E. coli cells; Lane D: recombinant IFN-β1 of CHO cells (comparison).

EXAMPLE 7

Preparation of immunoadsorbent and affinity chromatography of IL-6 preparations

Ascitic fluids of mice, containing monoclonal antibodies secreted by hybridoma 34-1, were precipitated with ammonium sulfate (50% saturation) 16 hrs at 4° C. The precipitate was collected by centrifugation, redissolved in water and dialysed against saline. About 10 mg of immunoglobulins were bound to 1 ml agarose-polyacryl-hydrazide according to Wilcheck and Miron (1974) Methods Enzym. 34, p. 72. Crude preparations of either natural (fibroblast) or recombinant (E. coli or CHO) IL-6 (containing 0.5M NaCl) were loaded at 4° C. at a flow rate of 0.25 ml/min. The column was washed with 30 column volumes of 0.5M NaCl in PBS. IL-6 was eluted by 50 mM citric acid buffer, pH 2 (8×1 column volume fractions) and immediately neutralized by 0.1M Hepes buffer, pH 8.5.

Figure 6:
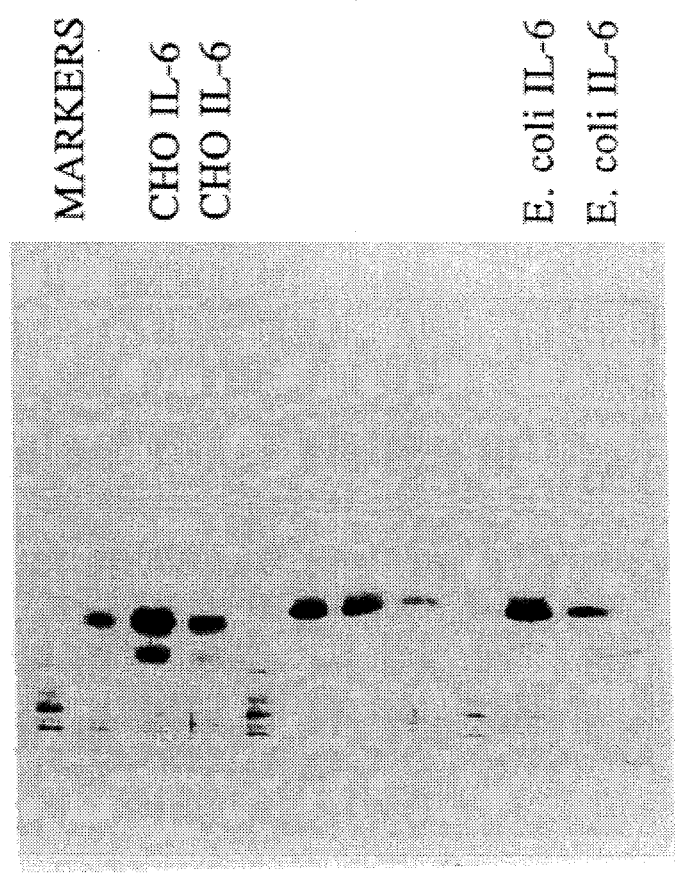
FIG. 6 shows the silver stain analysis of SDS-PAGE of the eluted fractions obtained from an anti-IL-6 column after being loaded with either crude recombinant IL-6 from *E. coli* or crude recombinant IL-6 from CHO.

Crude recombinant IL-6 (*E. coli* extract depleted from DNA) was loaded on 1 ml of the anti-IL-6 column. Purification of 1000 fold was achieved in one step, and the recovery of IL-6 was 100% (Table 2). The procedure was scaled up using 8 ml affinity column. The capacity of the column was 400 μg pure IL-6 per 1 ml of column. Silver stain analysis of SDS-PAGE of the eluted fractions revealed a major band of a M. W. of 21,000 and some minor contaminants of a higher M. W. (FIG. 6). When crude recombinant IL-6 (CHO) was loaded on 1 ml affinity column, purification was achieved in one step with a recovery of 100%. Silver stain analysis of SDS-PAGE of the eluted fractions revealed two bands of a M. W. of 23,000 and 28,00, both belonging to the glycosylated forms of IL-6 (FIG. 6). The same bands were obtained when natural IL-6 (foreskin fibroblasts) was immunoaffinity purified.

TABLE 2

| Source | Sample | HGF units/ml × $10^{-4}$ | Prot. conc. mg/ml | Spec. act. units/mg | Purif. fold | Recovery % |
|---|---|---|---|---|---|---|
| *E. coli* | load | 1.4 | 4.1 | 3400 | | |
| | Efluent | 0.54 | 4.1 | 1300 | | |
| | eluate | 25 | 0.09 | $3.6 \times 10^6$ | 1060 | 100 |
| CHO | load | 0.2 | | | | |
| | Efluent | 0.06 | | | | |
| | eluate | 2.7 | 0.14 | $0.2 \times 10^6$ | | 100 |
| Foreskin fibroblast | load | 0.014 | 1.46 | 95 | | |
| | Efluent | 0.014 | — | | | |
| | eluate | 0.014 | 0.008 | $17 \times 10^4$ | 180 | 100 |

EXAMPLE 8

Affinity chromatography of IL-6 produced by CHO cells

The quantitation of the IL-6 production in CHO cells, obtained by transfection with an SV40-IL-6 hybrid plasmid was made possible by the use of monoclonal antibody 34-1 for purification by immunoaffinity of the IL-6 produced and secreted in one liter of culture medium by one of the CHO clones.

Clone A2-5-10 is a CHO clone obtained by transfection of CHO cells with an SV40-IL-6 plasmid and selection with 50 nM MTX. This clone was grown to confluency in roller bottles. The culture medium was changed to a low (2%) fetal calf serum and collected 24 hours after the change.

One liter of culture was concentrated to 45 ml and loaded on the monoclonal antibody affinity column prepared in Example 7. The column was extensively washed and the bound IL-6 was eluted with 50 mM citric acid pH2, in four fractions of one ml each. The IL-6 purified in this way seems to be homogeneously pure as indicated by silver stain of polyacrylamide gel (FIG. 6). The amount of IL-6 protein recovered from one liter of culture was 469 μg.

Figure 7:
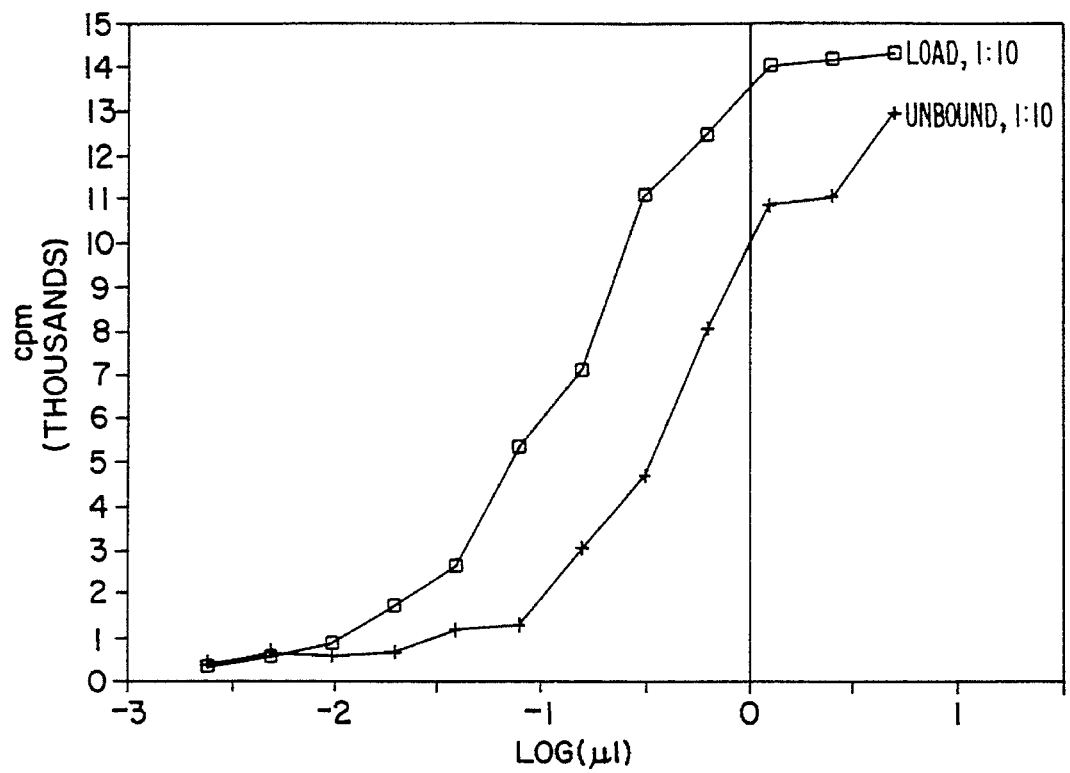
FIG. 7 is a graph showing the activity of IL-6 as loaded and as recovered from an affinity chromatography column in the unbound fraction.
Figure 8:
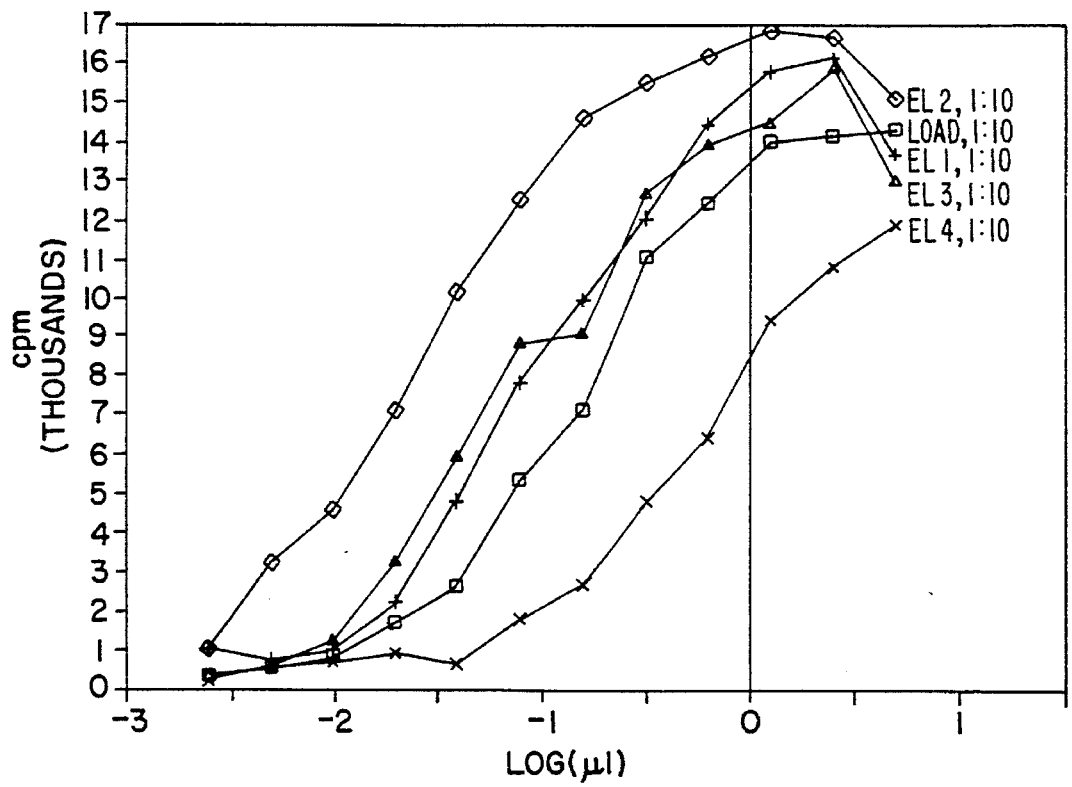
FIG. 8 is a graph showing the activity of IL-6 as loaded and as the various fractions eluted at pH 2 from an affinity chromatography column.

The amount of IL-6 in each fraction was estimated by measuring the hybridoma growth factor (HGF) activity of the protein in the crude preparation and in the different fractions of the affinity column. About 40% of the IL-6 loaded on the column was recovered in the unbound fraction (FIG. 7); the remaining activity was recovered in fractions eluted with pH2 (FIG. 8) with a peak in elution 2. These results indicate that; under the conditions described above, clone A2-5-10 produces about 800 μg/l of IL-6.

The specific activity of the IL-6 produced and secreted by the CHO clone A2-5-10 was determined by measuring the HGF activity and the protein concentration in each of the purified fractions of the immunoaffinity column. One unit of HGF is defined as the amount of protein that gives 50% of the maximal effect in the assay. The HGF activity was assayed in 0.1 ml cultures of murine plasmacytoma T1165 cells, treated for 24 hours and pulsed for 16 hours with [$^3$H]thymidine as described by Nordan R. P. and Potter M. (1986) Science 233, pp. 566–568. Table 3 summarizes the results of such an analysis which is based on the experimental results shown in FIG. 8.

The specific HGF activity of IL-6 in the three fractions, eluted from the affinity chromatography column, ranged from $1.18 \times 10^6$ to $2.1 \times 10^6$ with an average of $1.47 \times 10^6$.

TABLE 3

| | Specific Activity of IL-6 | | |
|---|---|---|---|
| Fraction | HGF activity U/ml | Protein concentration mg/ml | Specific activity U/ml |
| Elution 1 | 128,000 | 0.108 | $1.18 \times 10^6$ |
| Elution 2 | 333,000 | 0.239 | $1.39 \times 10^6$ |
| Elution 3 | 166,000 | 0.079 | $2.10 \times 10^6$ |
| Total | 627,000 | 0.426 | $1.47 \times 10^6$ |

The neutralizing activity of monoclonal antibody 34-1 produced by growing the hybridoma in an Acusyst system (immunoglobulin concentration: 300 μg/ml) was assayed in the HGF assay.

Figure 9:
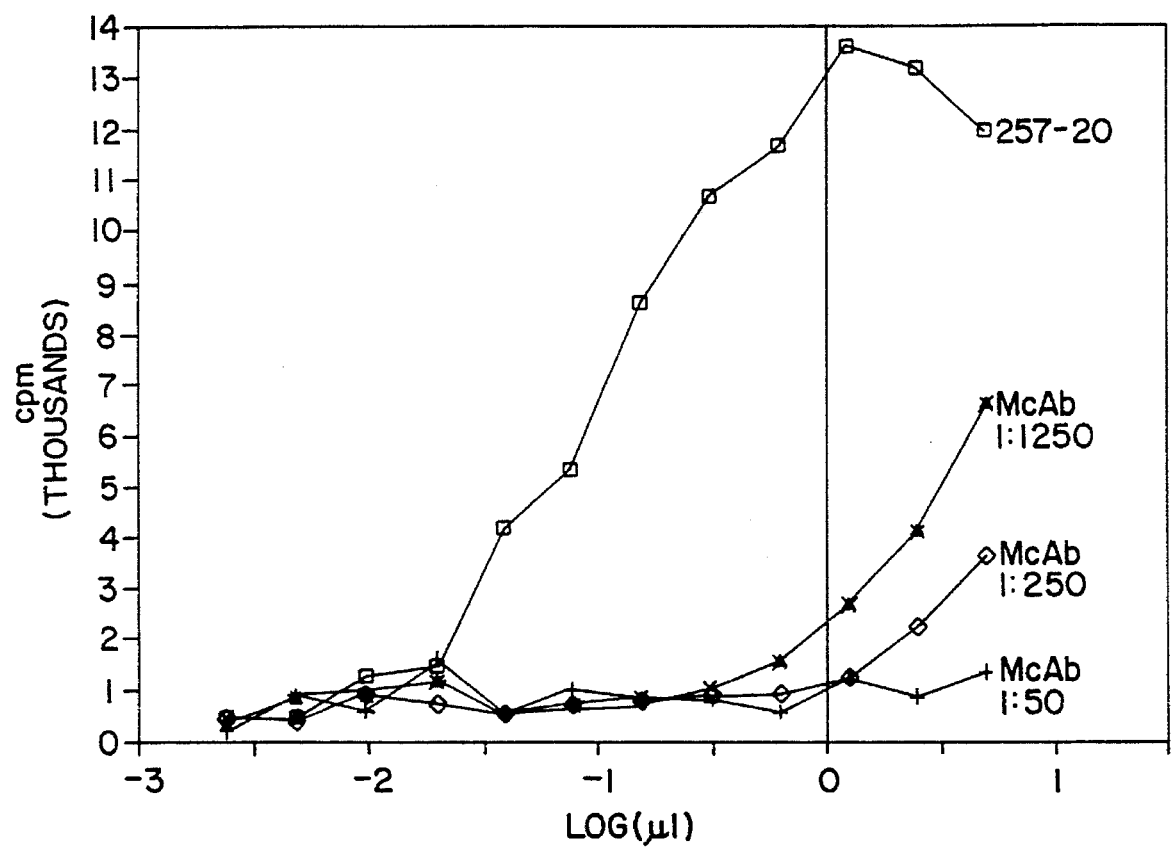
FIG. 9 is a graph showing an assay of IL-6 antibody activity in the presence of different dilutions of antibody.

In the experiment shown in FIG. 9, different dilutions of the antibody were introduced into the assay together with the IL-6 produced by CHO clone 257-20. At the highest dilution assayed (1:6,250) this antibody neutralizes one unit of HGF. Less diluted (1:250) antibody completely neutralizes 48 units of HGF (the highest amount used in the assay), while a 1:1,250 dilution of the antibody neutralizes only partially this amount of HGF. These results clearly indicate that the titer of the antibody preparation is around 6,000.

EXAMPLE 9

Purification of recombinant IL-6 produced by *E. coli* cells
a) Immunopurification

*E. coli* IL-6 was prepared according to Israeli Patent Application 85204. The first large scale purification (Experiment A4) started with 5.6 liters of culture or 1,400 ml of Dyno-mill extract. After polyethyleneimine precipitation, the solution was concentrated by PEG followed by Amicon YM10 filtration down to 100 ml (64 mg/ml). The material was loaded on an 8 ml column of monoclonal antibody 34-1 (Ig from ascites, 8 mg Ig/ml column) in phosphate buffered saline (PBS) with 0.5M NaCl pH 7.0. After washing the column with 50 volumes of the same buffer, elution was carried out by 50 mM citric acid buffer pH 2 and samples were immediately neutralized by addition of 0.1 m Hepes buffer pH 8.5. The results were as follows:

| A4: Immunopurification from 5.6 liter culture: | | | | | |
|---|---|---|---|---|---|
| FRACTION | Volume | Protein | HGF activity | HGF U/ml | HGF U/mg |
| LOAD ELUTED: | 90 ml | 5,700 mg | 29 million U | 325,000 | 5,100 |
| Total (Tube 3) | 40 ml 10 ml | 8.2 mg 2.2 mg | 2.9 million U | 110,000 | 500,000 |

A second large scale immunoaffinity column was run: Experiment A8. One liter of Dyno-mill extract (from 4 liter of fermentor culture) was treated by polyethyleneimine and concentrated to 500 ml, then dialysed against PBS-1M NaCl. This time the column was run in PBS-1M NaCl (instead of 0.5M NaCl in A4) and propylene glycol 25% was added to the citric acid pH 2 elution buffer. Samples were immediately neutralized by 0.1 m Hepes buffer pH 8.5. The results were as follows:

| A8: Immunopurification from an equivalent of 2.8 liters culture: | | | | | |
|---|---|---|---|---|---|
| FRAC-TION | Volume | Protein | HGF activity | HGF U/ml | HGF U/mg |
| LOAD | 350 ml | 2,550 mg | 10 million U | 330,000 | 4,100 |
| ELUTED: | | | | | |
| Total | 37 ml | 5.2 mg | 22 million U | | 4.2 million |
| (Tube 3) | 9.5 ml | 2 mg | | | 1.3 million | b) Final purification step following immunoaffinity

An S-Sepharose column was used as the final step. A typical experiment is described: Experiment S12.

The input was from A4 pooled fractions. The tubes were dialyzed against 10 mM acetate buffer pH 5, adsorbed and eluted by a gradient from 0.1–0.4M NaCl. The peak eluted at 0.3M. The results were as follows:

| S12: S-Sepharose after immunoaffinity | | | | | |
|---|---|---|---|---|---|
| FRAC-TION | Volume | Protein | HGF activity | HGF U/ml | HFG U/mg |
| INPUT: | | | | | |
| A4 pool | 17.5 ml | 3.6 mg | 1.4 million U | | 0.5 million |
| pH5 dial. | 22.5 ml | 2.2 mg | ND | | |
| ELUTED: | | | | | |
| Total peak | 4.5 ml | 0.6 mg | 0.9 million U | | 2 million |
| Tube 58 | 0.5 ml | 0.04 mg | | 210,000 | 5.2 million |

Figure 10:
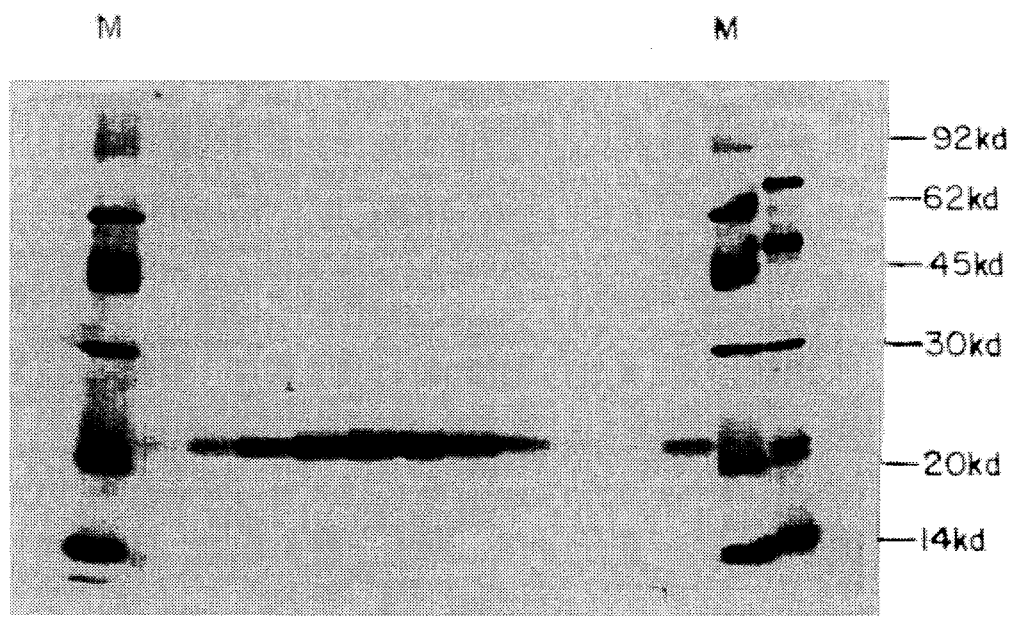
FIG. 10 shows the results of SDS-PAGE analysis of purified fractions of IL-6 from S-Sepharose.

The yield in this step was 64%. The product was run on SDS polyacrylamide gel under reducing and non-reducing conditions and showed one single band at 21 Kd. (FIG. 10).

An ELISA has been developed for the measurement of IL6 concentration which is based on competition between labeled and non-labeled IL6 for a binding to mAb 34.1 immobilized in ELISA plate wells. ELISA plates (e.g. CoBind plates) were coated with purified mAb 34.1 by (5 µg Ab/ml in PBS, for 3 hours at 37° C.). The plates were blocked by incubation with PBS containing 5% BSA, for 1 hour at ambient temperature.

Immunoaffinity purified IL6 was labeled with biotin (1 mg of IL6 were reacted with 100 µg of n-hydroxysuccin-imide-biotin, at pH 9.0, for 2 hours at ambient temperature). The free biotin was separated from the modified IL6 by a column of Sephadex G25.

1 µg of biotinylated IL6 together with test material were introduced into each well and the plates were incubated for 1 hour at 37° C., washed, and then incubated with a conjugate of extravidin (Sigma) conjugated with horseradish peroxidase for 15 minutes at ambient temperature.

Activity of the horseradish peroxidase was monitored by use of the colorigenic substrate o-phenylenediamine.

The working range of the assay is 31 to 500 ng IL6/ml. The limit of detection is 15.5 ng/ml. The limit of quantitation is 31 ng/ml. The assay is highly reproducible and is suitable for monitoring of IL6 concentration in the different manufacturing and purification steps.

Figure 11:
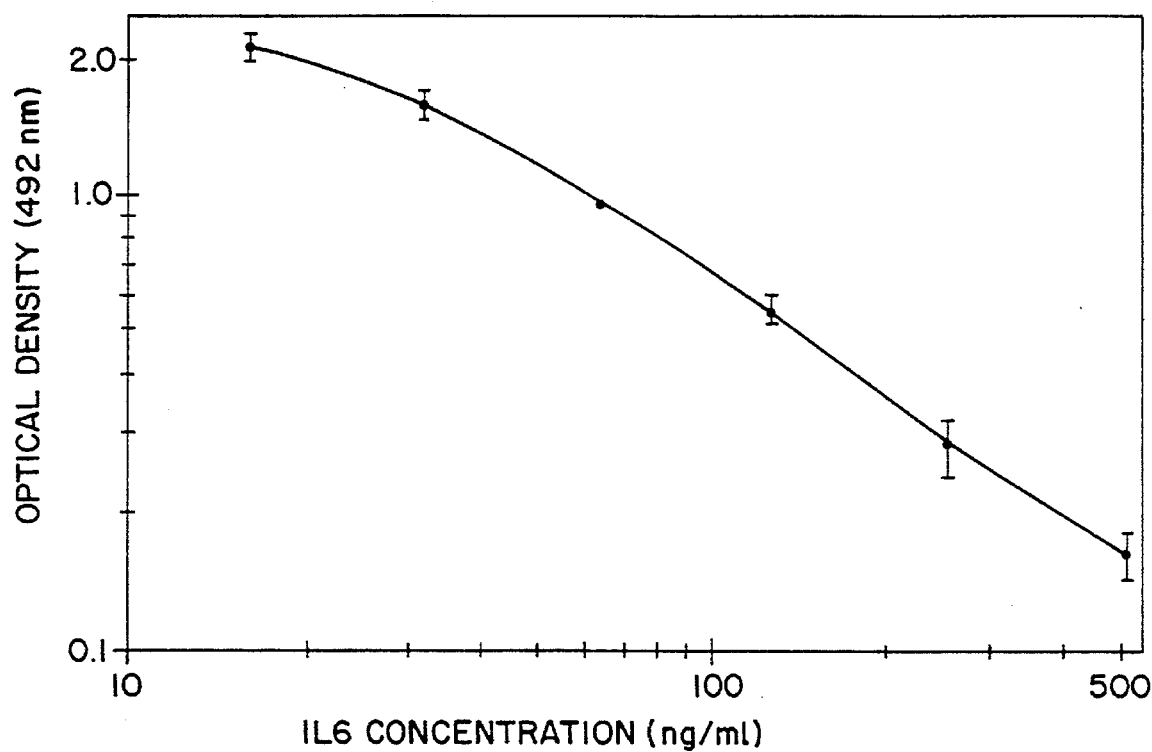
FIG. 11 is a graph showing the calibration curve of IL-6 concentration as a function of optical density in an ELISA assay.

A sample of the calibration curve is shown in FIG 11.

The purified IL-6 obtained by the present invention may be formulated in pharmaceutical compositions as described in European Patent Publication No. 220,574 and Israel: Patent Application No. 85204 and in copending Israel: Application No. 88376 filed on Nov. 14, 1988.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. The hybridoma cell line CNCM I-813 (No. 34-1).

2. A monoclonal antibody expressible by hybridoma cell line CNCM I-813 (HB2 34-1).

3. A method for producing anti-IL-6 monoclonal antibodies which comprises culturing hybridoma CNCM I-813 in a suitable growth medium and recovering the monoclonal antibodies from the supernatant of said hybridoma.

4. A method for producing anti-IL-6 monoclonal antibodies which comprises injecting hybridoma CNCM I-813 in a mouse and recovering the monoclonal antibodies from the ascitic fluid of said mouse.

5. A method for the immunopurification of human biologically active IL-6 comprising passing a sample containing human IL-6 through an immunoadsorbent column comprising a monoclonal antibody in accordance with claim 2 bound to a solid phase support, washing the column, and eluting IL-6 from the column.

* * * * *